United States Patent [19]

Mayol et al.

[11] Patent Number: 5,357,963
[45] Date of Patent: Oct. 25, 1994

[54] SEALED MAGNETIC DRIVE MEANS WITHOUT A PASSAGE THROUGH A WALL AND ULTRASOUND PROBE COMPRISING AN APPLICATION THEREOF

[75] Inventors: Jean-Claude Mayol, Quinssaines; Jérôme Piaton, Montluçon, both of France

[73] Assignee: Societe d'Applications Generales d'Electricite et de Mecanique Sagem, France

[21] Appl. No.: 35,929

[22] Filed: Mar. 23, 1993

[30] Foreign Application Priority Data

Mar. 23, 1992 [FR] France ............... 92 03463

[51] Int. Cl.⁵ .................. A61B 8/00; F16H 21/40
[52] U.S. Cl. .................. 128/660.1; 74/76; 74/DIG. 4
[58] Field of Search .......... 128/660.09, 660.1, 662.03; 74/26, DIG. 4; 310/103

[56] References Cited

U.S. PATENT DOCUMENTS

| | | | |
|---|---|---|---|
| 3,199,362 | 8/1965 | Pfeiffer | 74/DIG. 4 |
| 3,573,517 | 4/1971 | Osterstrom | 310/103 |
| 4,092,867 | 6/1978 | Matzuk | 73/609 |
| 4,486,176 | 12/1984 | Tardieu et al. | 74/DIG. 4 X |
| 4,524,623 | 6/1985 | Terwilliger | 74/26 |
| 4,732,156 | 3/1988 | Nakamura | 74/DIG. 4 X |

FOREIGN PATENT DOCUMENTS 0079284  11/1982  European Pat. Off. .
992852   3/1962   United Kingdom .

*Primary Examiner*—Francis Jaworski
*Attorney, Agent, or Firm*—Larso and Taylor

[57] ABSTRACT

The invention relates to a magnetic drive device enabling a member placed on one side of a non-magnetic wall to be driven by a rotary drive shaft placed on the other side of the wall. The driven member is mounted to rock about an oscillation axis orthogonal to the axis of rotation of the drive shaft and carries an axially-magnetized magnet whose outside surface has a right cross-section in the plane containing the oscillation axis and the axis of rotation of the drive shaft that is in the form of a circle centered on the oscillation axis. The drive shaft carries an axially-magnetized magnet offset from the axis of the drive shaft.

10 Claims, 2 Drawing Sheets

SEALED MAGNETIC DRIVE MEANS WITHOUT A PASSAGE THROUGH A WALL AND ULTRASOUND PROBE COMPRISING AN APPLICATION THEREOF

BACKGROUND OF THE INVENTION

The invention relates to magnetic drive devices enabling a member placed on one side of a non-magnetic wall to be driven from a rotary drive shaft placed on the other side of the wall.

Such devices are already in widespread use for transmitting rotary motion under conditions of total sealing. Both the drive shaft and the driven member which is constituted by a shaft that is coaxial with the drive shaft carry respective magnets. The two magnets tend to stay face-to-face, with the north pole of each of them being in alignment with the south pole of the other.

SUMMARY OF THE INVENTION

It is an object of the invention to provide a device that enables the driven member to have oscillating motion imparted thereto about an axis that is orthogonal to the axis of rotation of the drive shaft when the drive shaft rotates continuously.

To do this, the driven member is mounted so as to be rockable about an axis of oscillation that is orthogonal to the axis of rotation of the drive shaft and it carries an axially magnetized magnet whose outside surface has a right cross-section in the plane containing the oscillation axis and the axis of rotation of the drive shaft that is substantially in the form of a circle centered on the oscillation axis, the magnet carried by the drive shaft being magnetized axially and offset from the axis.

A particularly important (but not exclusive) application of the invention lies in ultrasound echography using a sector-scanning probe. Under such circumstances, the ultrasound probe which is generally immersed in a coupling liquid needs to have oscillating motion imparted thereto about an axis. At present, two solutions are used to achieve this object. Either the probe is driven by means of a rotary joint which is subject to wear, or else the drive mechanism is immersed in the coupling liquid. However, imprisoned or absorbed gases then run the risk of being given off in the form of bubbles that interfere with transmission through the coupling liquid.

These defects are avoided in the device of the invention.

The magnet carried by the driven member is generally in the form of a segment of a sphere with both the separating wall and the end surface of the magnet carried by the drive shaft being in the form of a spherical cap, thereby ensuring that the gap remains constant during motion. Nevertheless, in order to facilitate machining, it is possible for the magnet carried by the driven member to be in the form of a segment of a cylinder and/or to give the magnet carried by the drive shaft an end surface which is flat.

The invention also proposes an ultrasound probe, in particular for ophthalmological echography, comprising a device of the kind described above in which the driven member carries an ultrasound transducer placed in a space separated from the surrounding medium by said wall and by a window of material that has low ultrasound absorption.

The invention will be better understood on reading the following description of a particular embodiment, given by way of non-limiting example. The description refers to the accompanying drawings.

DESCRIPTION OF THE PREFERRED EMBODIMENT

Figure 1:
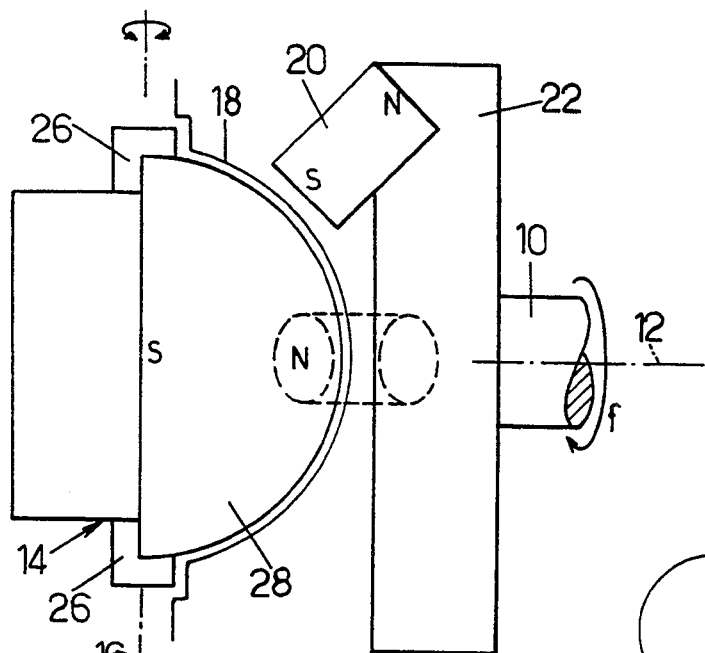
FIGS. 1 and 2 are theoretical diagrams respectively in elevation and in plan view showing the essential components of the device, with solid lines showing it in a middle position and with dashed lines showing it in a position of maximum deflection.
Figure 2:
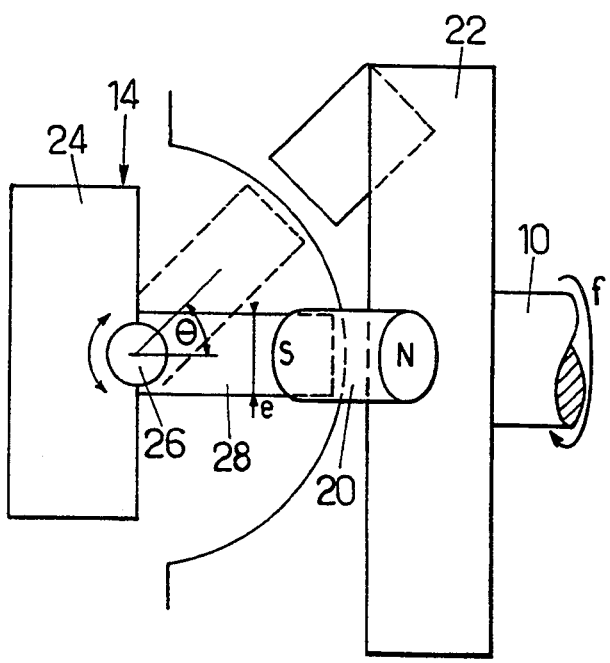

The magnetic drive device whose theoretical structure is shown in FIGS. 1 and 2 comprises a drive shaft 10 that is mounted to rotate about an axis 12 in the direction indicated by arrow f, and in the opposite direction. The drive shaft is intended to impart oscillating motion about an axis 16 orthogonal to the axis 12 to a driven member 14. The drive member 14 is separated from the shaft 10 by a thin wall 18 of non-magnetic material.

To do this, the drive shaft 10 carries a magnet 20 which, in the embodiment shown, is in the form of an axially-magnetized peg, offset from the axis, pointing towards the driven member, and fixed to a turntable 22 which is secured to the shaft 10. The magnet 20 has circular motion imparted thereto when the shaft 10 rotates, and it is advantageously placed in such a manner that its axis intersects the axis of rotation 12 at the point where it intersects the oscillation axis of rotation 16, or in the vicinity of said point of intersection.

The driven member shown comprises a body 24 fitted with two stub axles 26 that rotate in bearings (not shown) that define the oscillation axis 16. The body 24 carries a magnet 28 designed to move, following the magnet 20 in such a manner as to maintain a minimum gap between them. To do this, the midplane of the magnet 28, which must remain substantially in alignment with the midplane of the magnet 20, has a shape that is circular or nearly circular. In the example shown in FIG. 2, the magnet 28 is in the from of a segment of a cylinder. When the thickness e of the magnet is large, it is preferable for it to be in the form of a segment of a sphere, thereby enabling its surface to remain at a constant distance from the wall 18 which, generally speaking, is in the form of a spherical cap. For the same reason, it is advantageous for the end face of the magnet 20 to be in the form of a spherical cap when said magnet has a large diameter.

The operation of the device can be seen from the above description. When the shaft 10 rotates from an initial orientation in which the magnet 20 occupies the position shown in solid lines in FIGS. 1 and 2, it takes the magnet 28 progressively to the orientation θ (FIG. 2), and then causes the magnet 28 to rock in the opposite direction. As a result, continuous rotary motion of the shaft 10 causes the magnet 28 to oscillate through an angular amplitude of θ which is determined by the angle between the axis of the magnet 20 and the driving axis of rotation 12.

The above-described disposition makes it possible to avoid using any rotary joint which would be liable to suffer wear and which cannot be totally sealed, and to avoid using any membrane which is difficult to provide simultaneously with sufficient flexibility with sufficient strength and with sufficient chemical resistance to the media with which it is likely to come into contact.

Figure 3:
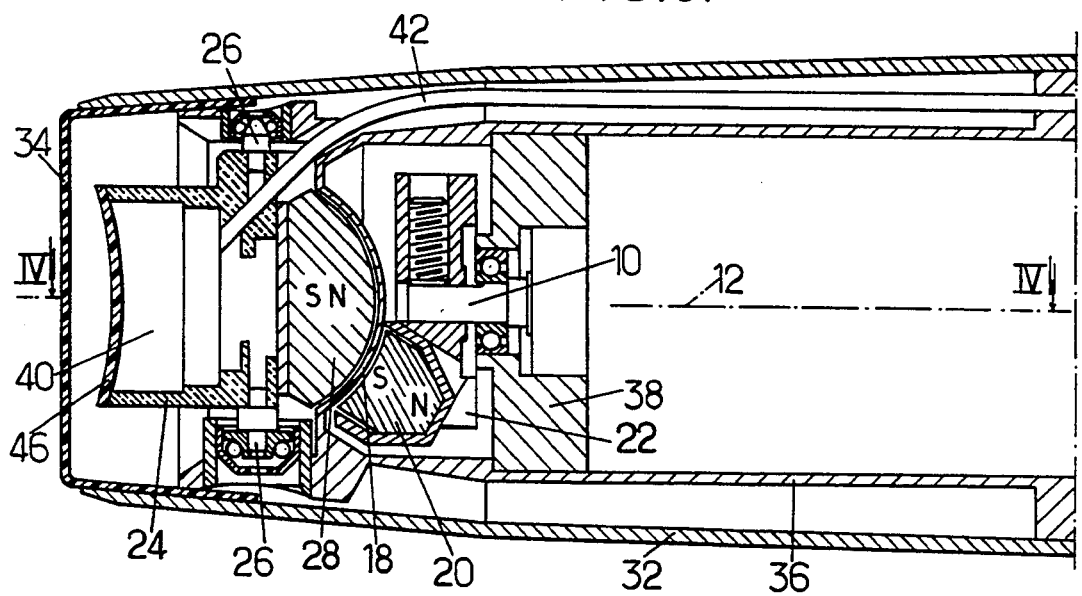
FIGS. 3 and 4 show an ultrasound probe incorporating one possible embodiment of the device, respectively in section on line III—III of FIG. 4 and on line IV—IV of FIG. 3.
Figure 4:
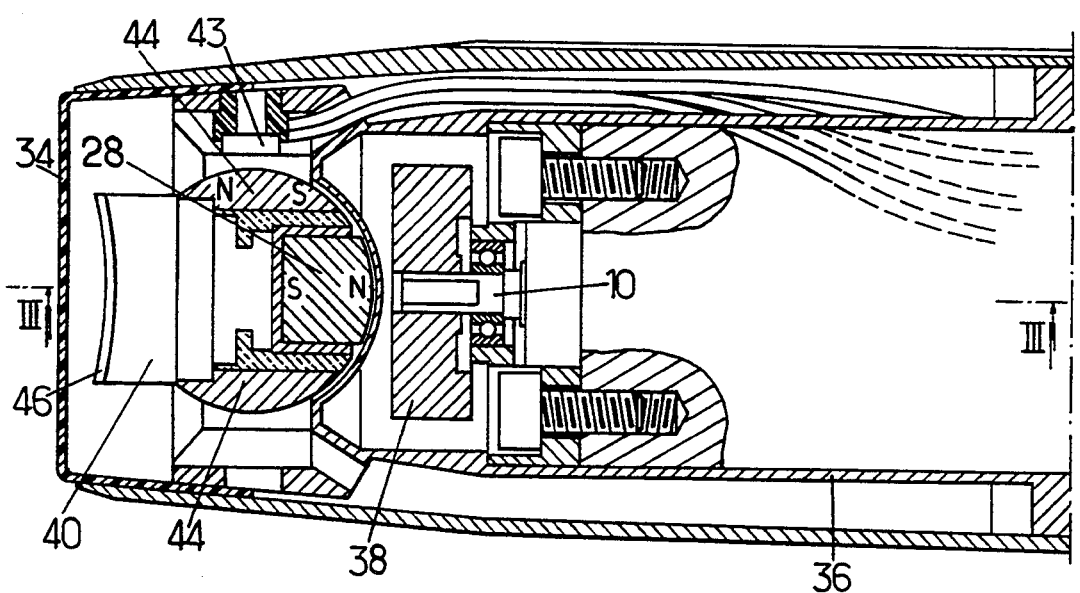

FIGS. 3 and 4 show the end portion of an ultrasound probe fitted with a device that complies with the diagrams of FIGS. 1 and 2, and members that correspond to those shown in FIGS. 1 and 2 are given the same reference numerals. The probe comprises a housing 32 closed by a window 34 designed to be applied against a member to be examined (e.g. an organ), generally via a gel for avoiding impedance discontinuities.

An envelope 36 concentric with the housing 32 receives the drive motor (not shown). A partition 38 installed transversely in the envelope 36 carries the shaft 10 via a ball bearing that defines the axis 12. The turntable 22 is installed on the shaft and carries the magnet 20. The end of the envelope 36 constituting the wall 18, and the facing face of the magnet 20 are both in the form of spherical caps.

The driven member comprises a body 24 fitted with stub axles 26 that rotate in two bearings carried on an extension of the envelope 36. The body 34 carries the magnet 28 whose outside surface is constituted by a segment of a sphere concentric with the wall 18. In general, the magnets are of the samarium-cobalt type, thereby enabling high torques to be transmitted.

A recess in the body 24 contains an ultrasound transducer, generally constituted by a piezoelectrical ceramic and connected to electronics (not shown) by means of a cable 42 that passes through the gap between the envelope 36 and the housing 32. A coupling liquid generally occupies the space delimited by the envelope 36, the housing 32, and the window 34.

Figure 5:
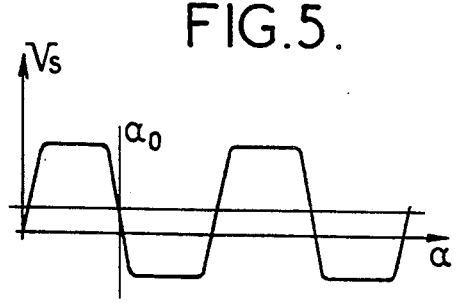
FIG. 5 is a diagram showing the appearance of the output voltage waveform Vs from a position sensor fitted to the device of FIGS. 3 and 4.

It is often necessary provide a sector probe with means enabling echoes in different firing directions to be displayed in their exact relative positions. Such means may include, in particular, a conventional incremental encoder (not shown) secured to the shaft 10. To enable absolute measurement to be made, the encoder is advantageously accompanied by a detector enabling a determined angular position of the probe to be sensed. For example, the detector may comprise a Hall-effect sensor 43 carried by the envelope, and a Hall-effect sensor exciting magnet 44 carried by the head. A second magnet 44 may be mounted symmetrically on the head for balance purposes. Since the Hall-effect sensor is subjected to the action of the magnet 20 in addition to that of the magnet 44, the output voltage from the sensor will generally vary as a function of the angle α between the driven member and its middle position or of the angle of rotation of the drive shaft in the manner shown in FIG. 5. The middle position can then be established by determining the angle of rotation of the shaft 10 at which the output voltage takes up a mean value.

Figure 6:
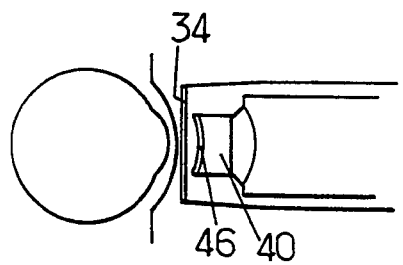
FIG. 6 is a diagram showing how an ultrasound probe of the kind shown in FIGS. 3 and 4 can be used in ophthalmology.

By way of example, there now follow the characteristics of an ultrasound probe that has been implemented for use in ophthalmology. Such a probe is intended to scan the eye in depth and it includes a single transducer 40 having a front face whose concave shape is such that pseudo-focusing takes place slightly in front of the retina when the window 34 is pressed against the eyelids, as shown diagrammatically in FIG. 6.

It is necessary to reduce impedance discontinuities to as small a value as possible, since they give rise to interfering absorption and reflection. For this purpose, the transducer 40 is covered by a thin membrane 46 that may be made of synthetic resin through which sound propagates at substantially the same velocity as through water, with the thickness thereof corresponding approximately to one-fourth of the wavelength of the ultrasound frequency used which is generally of the order of 10 MHz in order to improve resolution and penetration. The coupling liquid between the membrane 46 and the window 34 is selected so as to avoid chemically attacking the material constituting the window, so as to avoid being spoiled, and so as to have a sound propagation velocity comparable to the velocity in water. In particular, it is possible to use 1,2-propanediol in which the speed of sound is about 1490 meters per second (m/s) at body temperature. Finally, the window 34 is made of a material having low absorption, that ages slowly, that is non-irritant, and in which the sound propagation velocity is not too far from its propagation velocity in tissue. In particular, it is possible to use a thermoplastic material such as polymethylpentene, which absorbs ultrasound little and in which the speed of sound is about 2010 m/s.

When the window 34 is pressed against the eyelids via a continuity gel, the structure shown in FIGS. 3 and 4 makes it possible to achieve almost complete observation of the eye in depth, over a useful angle of about 50°.

We claim:

1. A magnetic drive device enabling a member placed on one side of a non-magnetic wall to be driven by a rotary drive shaft placed on the other side of the wall, comprising means carrying the driven member for rocking movement thereof about an oscillation axis that is orthogonal to an axis of rotation of the drive shaft, an axially-magnetized magnet securely connected to said driven member and having an outside surface which has a cross-section in a plane containing said oscillation axis and said axis of rotation of the drive shaft that is part circular and centered on said oscillation axis, and an axially-magnetized magnet fixed to said drive shaft and offset from said axis of rotation.

2. A device according to claim 1, wherein the magnet carried by the drive shaft is in the form of a substantially cylindrical peg with its axis pointing towards the center of the circle.

3. A device according to claim 2, wherein the face of the peg facing the center is in the form of a spherical cap.

4. A device according to claim 1, wherein the magnet carried by the driven member is in the form of a segment of a sphere or of a cylinder, and in that the separating wall is in the form of a spherical cap.

5. An ultrasound probe comprising a magnetic drive device enabling a member placed on one side of a non-magnetic wall to be driven by a rotary dive shaft placed on the other side of the wall, comprising means carrying the driven member for rocking movement thereof about an oscillation axis that is orthogonal to an axis of rotation of the drive shaft, an axially magnetized magnet securely connected to said driven member and having an outside surface which has a cross-section in the plane containing said oscillation axis and said axis of rotation of the drive shaft that is in the form of part of a circle centered on said oscillation axis, an axially-magnetized magnet fixed to said drive shaft and offset from said axis of rotation, and an ultrasound transducer carried by said driven member and placed in a space separated from the surrounding medium by said separation wall and by a window that has low ultrasound absorption.

6. A probe according to claim 5, wherein the probe includes means for measuring the angular position of the transducer, said means comprising an incremental encoder on the drive shaft and a detector for detecting a determined angular position of the transducer.

7. A probe according to claim 6, wherein the detector comprises a magnet fixed on the driven member and a stationary Hall-effect sensor.

8. A probe according to claim 5, wherein the transducer is covered by a thin membrane of synthetic resin having a thickness that corresponds approximately to one-fourth of the wavelength at the ultrasound frequency used.

9. A probe according to claim 5, wherein the window is made of a thermoplastic material and the gap is occupied by 1,2-propanediol.

10. A probe according to claim 5, for examining the eye, wherein the angle of oscillation is bout 50°.

* * * * *